US005637730A

United States Patent [19]
Murthy et al.

[11] Patent Number: 5,637,730
[45] Date of Patent: Jun. 10, 1997

[54] SODIUM ENALAPRIL COMPLEX AND THE USE THEREOF TO MAKE SODIUM ENALAPRIL

[75] Inventors: K. S. Keshava Murthy, Brantford; Andrew Burchat, Guelph; Gamini Weeratunga, Bantford, all of Canada

[73] Assignee: Brantford Chemicals Inc., Brantford, Canada

[21] Appl. No.: 699,338

[22] Filed: Aug. 19, 1996

[30] Foreign Application Priority Data

Jul. 29, 1996 [CA] Canada ................................. 2182258

[51] Int. Cl.$^6$ ................................. C07D 207/09
[52] U.S. Cl. ................ 548/540; 548/334.1; 548/402
[58] Field of Search ................................. 548/540

[56] References Cited

U.S. PATENT DOCUMENTS 4,374,829  2/1983  Harris et al. ........................ 424/177

OTHER PUBLICATIONS

Med. Chem. Rev., 1985, 5, 483.

Adv. Drug Delivery Rev., 1992, 8, 253.

Drug Met. Dispos., 1982, 10, 15.

J. Pharm. Exp. Ther., 1981, 216, 552.

J. Pharm. Exp. Ther., 1983, 226, 192.

*Primary Examiner*—Johann Richter
*Assistant Examiner*—Laura R. Cross
*Attorney, Agent, or Firm*—Ivor M. Hughes

[57] ABSTRACT

A process for making pure sodium enalapril is provided which includes the step of decomplexing essentially pure sodium enalapril-sodium iodide complex to yield essentially pure sodium enalapril.

11 Claims, No Drawings

SODIUM ENALAPRIL COMPLEX AND THE USE THEREOF TO MAKE SODIUM ENALAPRIL

FIELD OF THE INVENTION

This invention relates to a process for making pure and stable sodium enalapril-sodium iodide complex which can be decomplexed to give pure sodium enalapril. This invention also relates to other sodium enalapril monovalent metal monovalent counterion complexes which can also be decomplexed to give pure sodium enalapril.

BACKGROUND OF THE INVENTION

Enalapril is a well-known ACE inhibitor. Its chemistry (*Medicinal Chem. Rev.*, 1985, 5, 483), preparation (U.S. Pat. No. 4,374,829), biological transport (*Advanced Drug Delivery Rev.*, 1992, 8, 253), active metabolites (*Drug Met. Dispos.*, 1982, 10, 15). Pharmacology (*J. Pharmacol. Exp. Ther*,. 1981, 216, 552), Bioavailability (*J. Pharmacol. Exp. Ther*, 1983, 226, 192), and clinical use in the treatment of hypertension have been reviewed.

Enalapril is typically isolated and purified as the maleate addition salt. Another salt of enalapril which could have pharmaceutically acceptable characteristics is the sodium salt. The sodium salt of enalapril is not easily purified since it is soluble in most organic solvents and in water. In pure form, it is a hydroscopic oil or glass. Sodium enalapril can be prepared by treating the maleate with a sodium alkoxide or sodium hydroxide and selectively crystallizing the disodium salt of maleic acid. The solutions containing pure sodium enalapril thus obtained often contain trace amount of the base used to form the salt. Sodium enalapril undergoes a very facile ester hydrolysis in aqueous media in the presence of base to generate sodium enalaprilat, which is not orally active. Commercial production of pure sodium enalapril is thus very difficult.

It is therefore an object of this invention to provide improved processes for the manufacture of sodium enalapril and intermediates thereof.

It is a further object to provide intermediates suitable for use to manufacture sodium enalapril.

Further and other objects of the invention will be realized by those skilled in the art from the following summary of the invention and detailed description of embodiment.

SUMMARY OF INVENTION

During our attempts to make sodium enalapril, conditions which would minimize trace amounts of strong bases and organic media most likely to facilitate the precipitation of a sodium salt were investigated. One of these approaches involved the formation of the tetrabutylammonium salt of enalapril which was then treated with sodium iodide. The resulting mixture underwent an ion exchange and a precipitate was formed. The resulting precipitate was not the expected sodium enalapril but surprisingly a sodium iodide-sodium enalapril complex. The complex can then be purified by recrystallization and handled easily. The pure sodium iodide complex of sodium enalapril is then decomplexed by for example an ion exchange with tetraalkylammonium chlorides and subsequent selective precipitation of the sodium chloride and tetraalkylammonium iodide. The sodium iodide-sodium enalapril complex thus provides a method of obtaining pure sodium enalapril under very mild conditions easily carried out on a commercial scale.

Thus according to one aspect of the invention, a process for making pure sodium enalapril includes (comprises) the step of decomplexing essentially pure sodium enalapril-sodium iodide complex to yield essentially pure sodium enalapril. (IIIA) According to another aspect of the invention, the manufacture of the sodium enalapril-sodium iodide complex comprises reacting crude sodium enalapril with sodium iodide to yield the sodium enalapril-sodium iodide complex. This complex can be easily purified.

The purified sodium enalapril-sodium iodide complex can then be decomplexed to produce the pure sodium enalapril, for example in an organic solution.

The sodium enalapril can be made by reacting I with 1,1'-carbonyldiimidazole (CDI) to form anhydride (II) which is reacted with the sodium salt of L-Proline to produce crude sodium enalapril III.

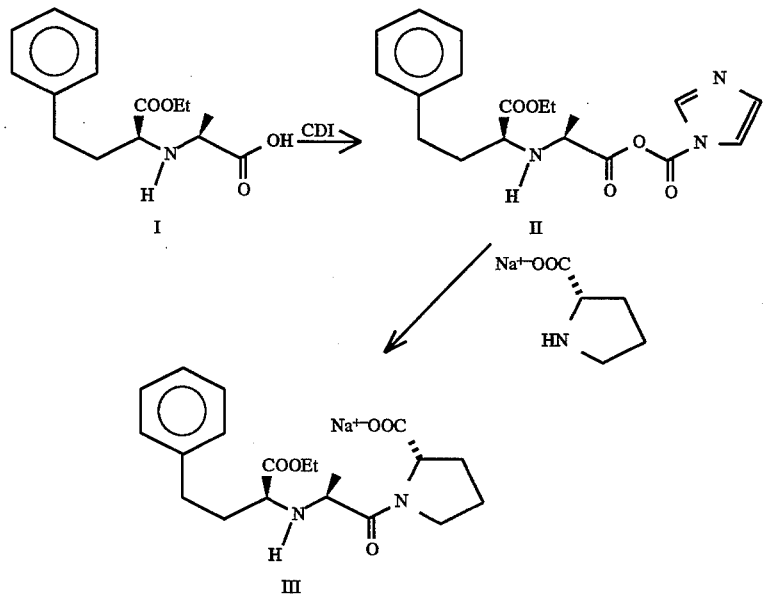

Crude enalapril III may react with sodium iodide to produce essentially pure sodium enalapril iodide complex (IV). The decomplexation of the essentially pure sodium enalapril-sodium iodide complex (IV) may be accomplished by

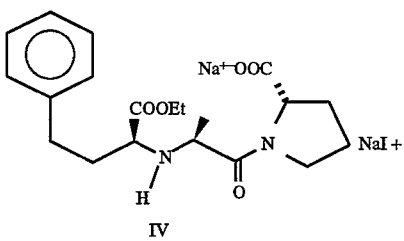

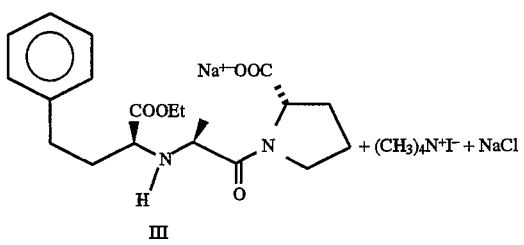

The sodium enalapril-sodium iodide complex (IV) has been found to be the preferred compound for this reaction. However, other complexes as would be apparent to persons skilled in the art are meant to be incorporated in this process. Such complexes would be manufactured in accordance with the teachings herein appropriately modified to make the desired complex.

DETAILED DESCRIPTION OF THE EMBODIMENTS

An Embodiment provides a new method for the production of sodium enalapril. (S)-N-(1-Ethoxycarbonyl-3-phenylpropyl)-L-alanine (I) is reacted with 1,1'-carbonyldiimidazole (CDI) to form the anhydride (II) which is reacted in an aprotic solvent with the sodium salt of proline to afford crude sodium enalapril (III) (75% yield).

Purification of the crude sodium enalapril (III) is conveniently achieved by the addition of one equivalent mole of sodium iodide to a solution of crude sodium enalapril in an alcohol such as ethanol or isopropanol which results in the formation of a 1:1 complex of sodium enalapril.sodium iodide (IV) for which is only slightly soluble in the alcohol used. Excess sodium iodide, as well as impurities associated with the synthesis of sodium enalapril, will remain dissolved in the alcohol and the pure solid complex ((IV) ¯greater than (99%) purity), may be separated by filtration. Final purification of the complex is achieved by recrystallization from the alcohol used or a water-alcohol mixture.

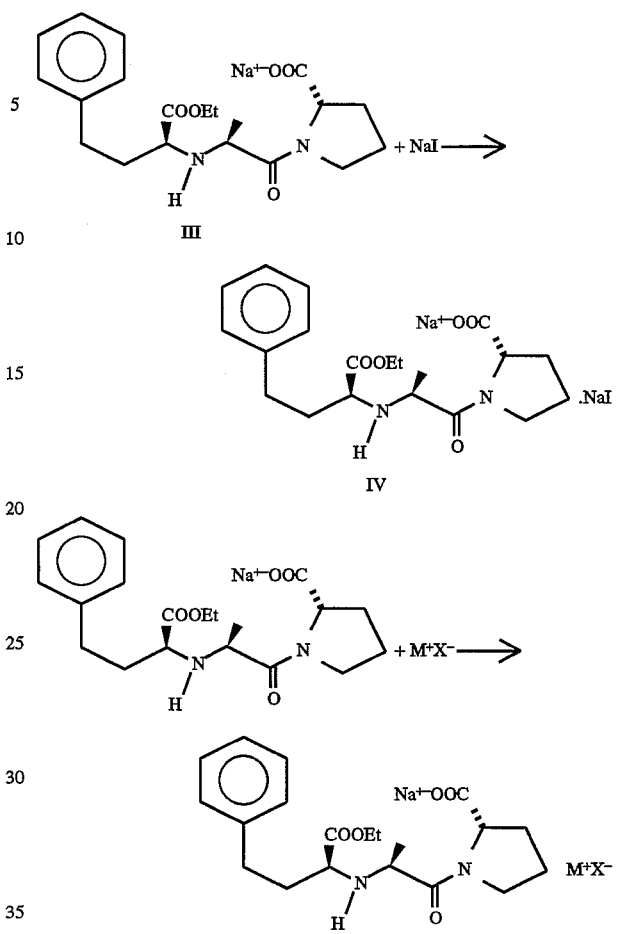

(where for example M is Metal Ion and X is Halogen)

Quantitative removal of sodium iodide from the complex can be achieved in a heterogeneous mixture of solvents consisting of a hydrophobic solvent such as toluene and a protic solvent such as water. The latter is removed by azeotropic distillation, causing precipitation, for example of tetramethylammonium iodide and sodium chloride. Sodium enalapril remains dissolved in toluene and can be separated from precipitated salts by filtration, resulting in a clear solution that contains the pure sodium enalapril. Although other tetraalkylammonium chlorides and other compounds as would be understood herein by persons skilled in the art may be used as well, the use of tetramethylammonium chloride is preferred since the resulting salts, namely tetramethylammonium iodide and sodium chloride, are very insoluble in hydrocarbon solvents.

Enalapril maleate is a very stable solid at room temperature, less than 2% degradation can be induced by storage at 80° C. for three weeks (*Analytical Profiles of Drug Substances,* 1987, 16, 207). The sodium enalapril-sodium iodide complex is also a stable solid at room temperature. HPLC analysis indicates less than 0.5% degradation by storage at 80° C. for three weeks.

A 1 mg/mL aqueous solution of sodium enalapril obtained by decomplextion of the sodium iodide complex generates less than 0.2% enalaprilat after 4 hours at room temperature.

EXAMPLE 1

Sodium Enalapril.Sodium Iodide Complex. (S)-N-[1-(S)-ethoxycarbonyl-3-phenylpropyl]-L- alanine (60 g, 0.215 mol) is suspended in 470 mL ethyl acetate and treated with 1,1'-carbonyldiimidazole (41.85 g, 0.258 mol). The mixture was stirred at room temperature for 1 hour. Sodium salt of L-Proline (29.46 g, 0.215 mol) was added and stirring was continued for 3 hours. The reaction mixture was filtered over Celite (15 g) and washed with ethyl acetate (3×20 mL). The filtrate was concentrated under vacuum to give an oil which was dissolved in isopropyl alcohol (2.6 L) and treated with sodium iodide (32.26 g, 0.215 mol). The mixture was heated to reflux to afford a clear solution which was cooled to room temperature and then to 5° C. for 2 hours. The resulting white precipitate was filtered and washed with isopropanol and dried under vacuum at 40° C. to a constant weight of 81.55 g, 69.2%. The product may be further purified by recrystallization from isopropanol.

$^1$H NMR (300 MHZ, D$_2$O): (ppm) 1.00 (d, 3H, J=7.4 Hz), 1.05 (t, 3H, J=7.2 Hz), 1.68–2.10 (m, 6H), 2.47 (t, 2H, J=7.4 Hz PhCH$_2$), 2.94 (t, 0.7H), 3.11 (t, 0.3H), 3.20–3.28 (m, 1H), 3.37–3.42 (m, 2H), 3.93 (q, 2H, J=7.1 Hz), 4.00–4.04 (dd, 1H), 7.05–7.19 (m, 5H, Ar). $^{13}$C NMR (75 MHZ, DMSO-$d_6$): 171.2, 173.4, 174.0 (C=O), 141.5/141.9 (Ar), 128.1, 128.2, 128.3 (Ar), 125.5 (Ar), 58.4/58.6, 60.9/61.5, 59.7 (CH$_3$CH$_2$O), 52.3, 45.7, 34.7, 22.1, 29.1, 31.1, 18.5 (CH$_3$), 14.0 (CH$_3$CH$_2$O). IR (KBr): (cm$^{-1}$) 3426 (NH), 2874–2966 (Ar), 1730 (C=O ester), 1684 (C=O), 1646 (C=O).

EXAMPLE 2

Sodium Enalapril. Sodium enalapril.sodium iodide complex (100 g, 0.182 mole) and tetramethylammonium chloride (20 g, 0.182 mole) were ground to a powder and transferred with stirring to a flask containing 1000 mL toluene. To the mixture was added 40 mL water and stirring was continued for 15 minutes. Water was removed by azeotropic distillation under vacuum (Dean-Stark apparatus). The resulting heterogeneous mixture was cooled to 15° C. and filtered over a bed of Celite. Solvent was removed under reduced pressure from the clear filtrate followed by drying of the resulting oil under high vacuum at 55° C. for 24 hours to afford 72 g (99.4%) of a foam.

As many changes can be made to the embodiments and examples as would be understood by persons skilled in the art without departing from the scope of the invention, it is understood that all material contained herein be interpreted as illustrative of the invention and not in a limiting sense.

The embodiment of the invention in which an exclusive property or privilege is claimed are as follows:

1. A process for making pure sodium enalapril, said process comprising the step of decomplexing essentially pure sodium enalapril-sodium iodide complex to yield essentially pure sodium enalapril.

2. The process of claim 1 wherein manufacturing the essentially pure sodium enalapril-sodium iodide complex is made by reacting crude sodium enalapril with sodium iodide to yield a sodium enalapril-sodium iodide solid.

3. A process for manufacturing a sodium enalapril-sodium iodide complex comprising reacting crude sodium enalapril with sodium iodide to yield sodium enalapril-sodium iodide complex.

4. The process of claim 3 wherein the sodium enalapril-sodium iodide complex is decomplexed to produce sodium enalapril.

5. The process of claim 4 wherein the process is carried out in an organic solvent.

6. The process of claim 1 or 2 wherein sodium enalapril can be made by reacting

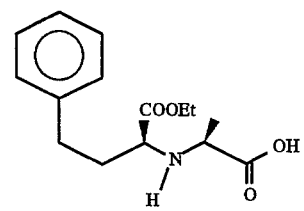

with 1,1'-carbonyldiimidazole (CDI) to form anhydride II

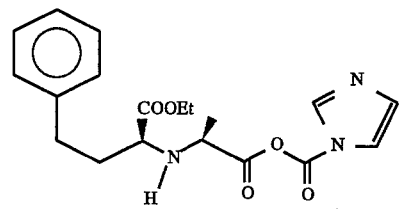

which is then reacted with the sodium salt of Proline to produce crude sodium enalapril III

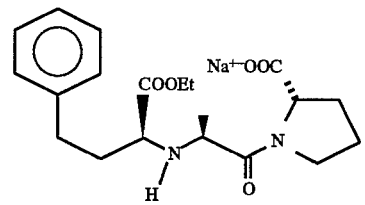

7. The process of reacting

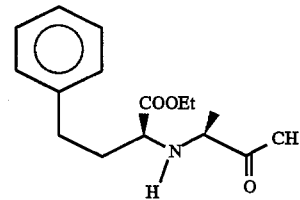

with 1,1'-carbonyldiimidazole (CDI) to produce

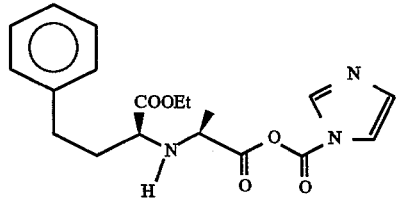

8. The process of reacting

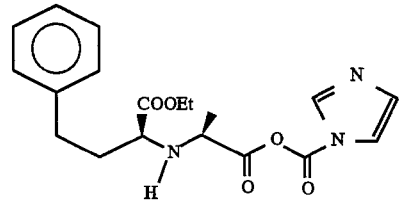

with

-continued
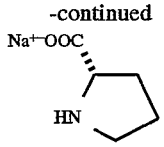
to produce
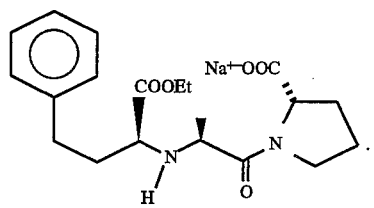
9. The Process of reacting
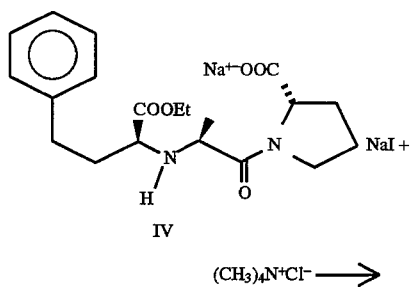
$(CH_3)_4N^+Cl^- \longrightarrow$
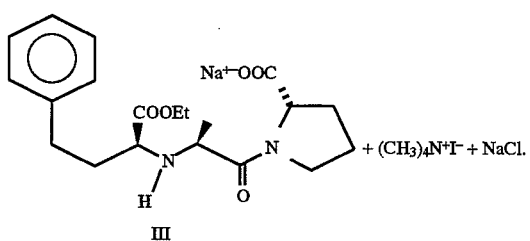
10. The process of reacting
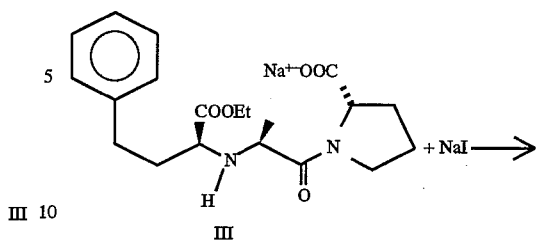
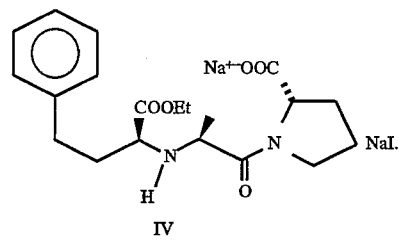
11. The process of reacting
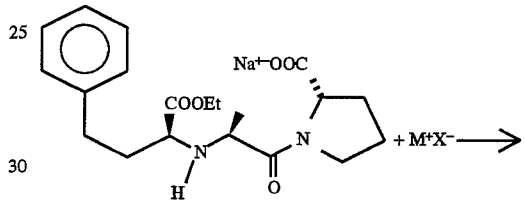
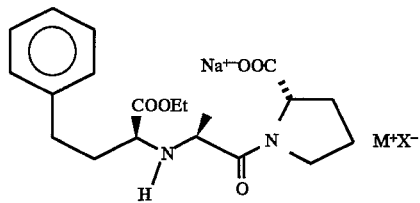
where X is halogen and M is Metal ion.
* * * * *